US007754870B2

(12) United States Patent
Oh et al.

(10) Patent No.: US 7,754,870 B2
(45) Date of Patent: Jul. 13, 2010

(54) **METHOD AND COMPOSITIONS FOR DETECTING *HELICOBACTER PYLORI***

(75) Inventors: Ji-young Oh, Yongin-si (KR); Jung-nam Lee, Yongin-si (KR)

(73) Assignee: Samsung Electronics Co., Ltd. (KR)

( * ) Notice: Subject to any disclaimer, the term of this patent is extended or adjusted under 35 U.S.C. 154(b) by 374 days.

(21) Appl. No.: 11/742,111

(22) Filed: Apr. 30, 2007

(65) Prior Publication Data
US 2008/0076127 A1 Mar. 27, 2008

(30) Foreign Application Priority Data
Sep. 26, 2006 (KR) ...................... 10-2006-0093667

(51) Int. Cl.
*C12Q 1/68* (2006.01)
*A61B 17/22* (2006.01)

(52) U.S. Cl. ................ 536/24.33; 536/23.7; 536/24.32; 422/61; 435/6

(58) Field of Classification Search ........................ None
See application file for complete search history.

(56) References Cited

U.S. PATENT DOCUMENTS

| | | | |
|---|---|---|---|
| 2001/0019834 A1* | 9/2001 | Kim et al. ................... | 435/69.2 |
| 2003/0175746 A1 | 9/2003 | Quint et al. | |
| 2004/0048353 A1* | 3/2004 | Covacci et al. ............ | 435/252.3 |
| 2005/0276819 A1* | 12/2005 | Covacci et al. ............ | 424/234.1 |
| 2006/0003350 A1 | 1/2006 | Tsang et al. | |
| 2006/0193866 A1* | 8/2006 | Meinke et al. ............ | 424/164.1 |

OTHER PUBLICATIONS

Zhang, Y et al, Journal of Clinical Microbiology, Feb. 2005, vol. 43(2), pp. 786-790, Tyrosine Phosphorylation of CagA from Chinese *Helicobacter pylori* Isolates in AGS Gastric Epithelial Cells.*
Con, Sergio A et al, J. Gastroenterology, Jul. 2006, vol. 41, pp. 632-637, *Helicobacter pylori* CagA status associated with gastric cancer incidence rate variablity in Costa Rican regions.*
Yamaoka, Yoshio et al, Gastroenterology, 1999, vol. 117, pp. 342-349, Relationship between the cagA 3' Repeat Region of *Helicobacter pylori*, Gastric Histology and Susceptibility to Low pH.*
Owen, R.J. et al, Journal of Clinical Microbiology, Jul. 2003, vol. 41(7), pp. 3112-3118.*
Occhialini, A et al, Infection and Immunity, Mar. 2001, pp. 1902-1908, vol. 69(3), Composition and gene expression of the cag Pathogenicity Island in *Helicobacter pylori* strains isoalted from Gastric Carcinoma and Gastritis Patients in Cost Rica.*
Hatakeyama, M, Nature, Sep. 2004, vol. 4, pp. 688-694, Oncogenic mechanisms of the *Helicobacter pylori* CagA protein.*
Yamaoka, Y et al, Jouranl of Clinical Microbiology, vol. 36(8), Aug. 1998, pp. 2258-2263, Variants of the 3' region of the cagA gene in *Helicobacter pylori* Isolates from Patients with Different *H. pylori* associated diseases.*
NCBI, GenBank Accession No. AB057095, Jan. 12, 2006.
NCBI Accession No. AF89464, Mar. 7, 2001.

* cited by examiner

*Primary Examiner*—Robert B Mondesi
*Assistant Examiner*—Ginny Portner
(74) *Attorney, Agent, or Firm*—Cantor Colburn LLP

(57) ABSTRACT

Provided are an oligonucleotide primer set for amplifying at least one target sequence of the cagA gene of *Helicobacter pylori*, a method of detecting *Helicobacter pylori* using the primer set, and a kit for detecting *Helicobacter pylori*, including the primer set.

10 Claims, 2 Drawing Sheets

SEQUENCE LISTING

<160> NUMBER OF SEQ ID NOS: 9

<210> SEQ ID NO 1
<211> LENGTH: 22
<212> TYPE: DNA
<213> ORGANISM: Artificial Sequence
<220> FEATURE:
<223> OTHER INFORMATION: Primer Hpy-cagA-F1

<400> SEQUENCE: 1
aagttgatga tctcagtaag gt                                              22

<210> SEQ ID NO 2
<211> LENGTH: 21
<212> TYPE: DNA
<213> ORGANISM: Artificial Sequence
<220> FEATURE:
<223> OTHER INFORMATION: Primer Hpy-cagA-R1

<400> SEQUENCE: 2
tgctttagct tctgataccg c                                               21

<210> SEQ ID NO 3
<211> LENGTH: 22
<212> TYPE: DNA
<213> ORGANISM: Artificial Sequence
<220> FEATURE:
<223> OTHER INFORMATION: Primer Hpy-cagA-F2

<400> SEQUENCE: 3
gatgatctca gtaaggtagg gc                                              22

<210> SEQ ID NO 4
<211> LENGTH: 21
<212> TYPE: DNA
<213> ORGANISM: Artificial Sequence
<220> FEATURE:
<223> OTHER INFORMATION: Primer Hpy-cagA-R2

<400> SEQUENCE: 4
tctttgagct tgtctatcgt t                                               21

<210> SEQ ID NO 5
<211> LENGTH: 22
<212> TYPE: DNA
<213> ORGANISM: Artificial Sequence
<220> FEATURE:
<223> OTHER INFORMATION: Primer Hpy-cagA-F3

<400> SEQUENCE: 5
ttgatgatct cagtaaggta gg                                              22

<210> SEQ ID NO 6
<211> LENGTH: 22
<212> TYPE: DNA
<213> ORGANISM: Artificial Sequence
<220> FEATURE:
<223> OTHER INFORMATION: Primer  Hpy-cagA-R3

<400> SEQUENCE: 6
gaatctttga gcttgtctat cg                                              22

<210> SEQ ID NO 7
<211> LENGTH: 755
<212> TYPE: DNA
<213> ORGANISM: Helicobacter pylori

<400> SEQUENCE: 7
gcgttagccg atctcaaaaa tttctcaaag gagcaattgg cccaacaaac tcaaaaaaat     60
gaaagtttca atgttggaaa atctgaaata taccaatccg ttaagaatgg tgtgaatgga     120

-continued

```
accctggtcg gtaatgggtt atctcaagca gaagccacaa ctctttctaa aaacttttcg    180
gacatcaaga aagagttgaa tgcaaaactt ggaaatttca ataacaataa caataatgga    240
ctcaaaaacg aacccattta tgctaaagtt aataaaaaga aatcaggaca agcagctagc    300
cctgaagaac ccatttacgc tcaagttgct aaaaaggtga atgcaaaaat tgaccgactc    360
aatcaaatag caagtggttt gggtggtgta gggcaagcag cgggcttccc tttgaaaagg    420
catgataaag ttgatgatct cagtaaggta gggcgatcgg ttagccctga acccatttat    480
gctacaattg atgatctcgg cggacctttc cctttgaaaa ggcatgataa agttgatgat    540
ctcagtaagg tagggcgatc aagggagcaa gaattgactc agaaaattga caatctcagt    600
caagcggtat cagaagctaa agcaggtttt tttggcaatc tagaacaaac gatagacaag    660
ctcaaagatt ctacaaaaaa caattctatg aatctatggg ctgaaaatgc aaaaaagtg     720 cctgctagtt tgtcagcgaa actagacaat tacgc                              755
```

```
<210> SEQ ID NO 8
<211> LENGTH: 20
<212> TYPE: DNA
<213> ORGANISM: Artificial Sequence
<220> FEATURE:
<223> OTHER INFORMATION: forward primer for 16S rRNA

<400> SEQUENCE: 8
yccakactcc tacgggaggc                                                20

<210> SEQ ID NO 9
<211> LENGTH: 22
<212> TYPE: DNA
<213> ORGANISM: Artificial Sequence
<220> FEATURE:
<223> OTHER INFORMATION: reverse primer for 16S rRNA

<400> SEQUENCE: 9
gtgccagcag yygcggtaat ac                                             22
```

METHOD AND COMPOSITIONS FOR DETECTING *HELICOBACTER PYLORI*

This application claims priority from Korean Patent Application No. 10-2006-0093667, filed on Sep. 26, 2006, the disclosure of which is incorporated herein in its entirety by reference.

BACKGROUND OF THE INVENTION

1. Field of the Invention

The present invention relates to an oligonucleotide primer set for amplifying at least one target sequence of the cagA gene of *Helicobacter pylori* (*H. pylori*), a method of detecting *H. pylori* using the primer set, and a kit for detecting *H. pylori*, including the primer set.

2. Description of the Related Art

*Helicobacter pylori* (*H. pylori*) (formerly known as *Campylobacter pylori*) is a gram-negative bacterium that colonizes human gastric mucosa. *H. pylori* is frequently detected from gastric biopsy samples derived from patients suffering from gastritis and gastric ulcers. Epidemiological studies have shown that *H. pylori* is a causative substance for gastritis, gastric ulcers, and duodenal ulcers and is associated with diseases such as stomach cancer.

Once it colonizes gastric mucosa, *H. pylori* survives in the stomach and cannot be eradicated without medical treatment. Colonization of the gastric mucosa with *H. pylori* leads to type B chronic gastritis. *H. pylori* infection is responsible for 85% of chronic gastritis cases.

The infection route of *H. pylori* has not yet been firmly established, but it has been reported that *H. pylori* infection occurs when water or food in the vomit and feces of infected people is ingested through the mouths of other people or when the vomit and feces of infected people spread from person to person via flies. It has also been reported that *H. pylori* directly spreads from person to person through the oral-oral route. It has been reported that 50% or more of the Korean population are infected with *H. pylori*, and the infection rate rapidly increases with age (although it varies according to regional areas or occupation): 50-60% in adults, 1.1% in children aged under 5 years, 12.8% in children aged 5-9 years, and 20.4% in children aged 10-14 years.

When humans are infected with *H. pylori*, various upper gastrointestinal lesions can be caused according to the diversity of the *H. pylori* strains and the sensitivity of the infected humans. Most people infected with *H. pylori* do not show any symptoms immediately after infection but develop symptoms gradually.

In this regard, early diagnosis of *H. pylori* infection is very important in prevention or treatment of various gastric diseases. For this, it is necessary to rapidly and reproducibly detect even a small quantity of gene products produced by *H. pylori* at an initial stage of *H. pylori* infection.

U.S. Patent Publication No. 2003/0175746 discloses a method of detecting *H. pylori* in a biological sample and its related primers. U.S. Patent Publication No. 2006/0003350 discloses a method of detecting *H. pylori* in a biological sample, a diagnostic kit, and their related primers.

According to a conventional method of detecting *H. pylori*, mucosal biopsy samples are collected and cultured. However, problems arise in that *H. pylori* is irregularly distributed in the gastric surface mucosa, it is difficult to collect mucosal biopsy samples, and isolated epithelial cells from infected people are not efficiently cultured. Saliva samples can also be used for the detection of *H. pylori*. It has been demonstrated that the sensitivity of diagnosis of *H. pylori* infection using saliva samples is comparable to that of conventional diagnosis of *H. pylori* infection using other standard samples. However, *H. pylori* coexists with several hundreds of kinds of oral flora in saliva. Thus, in order to use a nucleic acid detection method, it is necessary to develop a marker capable of discriminating *H. pylori* from other oral flora.

While searching for a method of detecting *H. pylori* based on the above-described conventional techniques, the present inventors found that *H. pylori* can be specifically detected in saliva containing *H. pylori* and other oral flora using a primer set capable of amplifying at least one target sequence of the cagA gene of *H. pylori*, and thus, completed the present invention.

SUMMARY OF THE INVENTION

The present invention provides a primer set capable of amplifying target sequence(s) of the cagA gene of *Helicobacter pylori* (*H. pylori*).

In an embodiment, the oligonucleotide primer set comprises an oligonucleotide consisting of at least 10 contiguous nucleotides present in a nucleotide sequence as set forth in SEQ ID NO: 1 and an oligonucleotide consisting of at least 10 contiguous nucleotides present in a nucleotide sequence as set forth in SEQ ID NO: 2; an oligonucleotide set comprising an oligonucleotide consisting of at least 10 contiguous nucleotides present in a nucleotide sequence as set forth in SEQ ID NO: 3 and an oligonucleotide consisting of at least 10 contiguous nucleotides present in a nucleotide sequence as set forth in SEQ ID NO: 4; or an oligonucleotide set comprising an oligonucleotide consisting of at least 10 contiguous nucleotides present in a nucleotide sequence as set forth in SEQ ID NO: 5 and an oligonucleotide consisting of at least 10 contiguous nucleotides present in a nucleotide sequence as set forth in SEQ ID NO: 6.

The present invention also provides a method of detecting *H. pylori*.

In an embodiment, the method comprises isolating genomic DNA from a sample; using the isolated genomic DNA as a template and an oligonucleotide primer set specific for amplifying an *H. pylori*-specific target sequence in an *H. pylori* cagA gene in an amplification reaction; and detecting *H. pylori* in the sample when the *H. pylori*-specific target sequence is amplified.

The present invention also provides a kit for detecting *H. pylori*, including the primer set.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

The present invention provides an oligonucleotide primer set for amplifying at least one target sequence of the cagA gene of *Helicobacter pylori* (*H. pylori*). The oligonucleotide primer set comprises an oligonucleotide set comprising an oligonucleotide comprising at least 10 contiguous nucleotides present in a nucleotide sequence as set forth in SEQ ID NO: 1 and an oligonucleotide comprising at least 10 contiguous nucleotides present in a nucleotide sequence as set forth in SEQ ID NO: 2; an oligonucleotide set comprising an oligonucleotide comprising at least 10 contiguous nucleotides present in a nucleotide sequence as set forth in SEQ ID NO: 3 and an oligonucleotide comprising at least 10 contiguous nucleotides present in a nucleotide sequence as set forth in SEQ ID NO: 4; or an oligonucleotide set comprising an oligonucleotide comprising at least 10 contiguous nucleotides present in a nucleotide sequence as set forth in SEQ ID NO: 5 and an oligonucleotide comprising at least 10 contiguous nucleotides present in a nucleotide sequence as set forth in SEQ ID NO: 6. In an embodiment, the oligonucleotide primer set comprises an oligonucleotide set comprising an oligonucleotide consisting of at least 10 contiguous nucleotides present in a nucleotide sequence as set forth in SEQ ID NO: 1 and an oligonucleotide consisting of at least 10 contiguous nucleotides present in a nucleotide sequence as set forth in SEQ ID NO: 2; an oligonucleotide set comprising an oligonucleotide consisting of at least 10 contiguous nucleotides present in a nucleotide sequence as set forth in SEQ ID NO: 3 and an oligonucleotide consisting of at least 10 contiguous nucleotides present in a nucleotide sequence as set forth in SEQ ID NO: 4; or an oligonucleotide set comprising an oligonucleotide consisting of at least 10 contiguous nucleotides present in a nucleotide sequence as set forth in SEQ ID NO: 5 and an oligonucleotide consisting of at least 10 contiguous nucleotides present in a nucleotide sequence as set forth in SEQ ID NO: 6.

The cagA gene of *H. pylori* is the gene expressing cytotoxic-associated protein A. The length of the cagA gene coding sequence available in GenBank varies for the different strains of *H. pylori*, but is 820 bp on average, primarily starting from the 3' end of the coding sequence. The target sequence of the primer set of the present invention can be at least one sequence of the cagA gene of *H. pylori* selected from nucleotide regions corresponding to positions 428-624, 433-668 and 431-671 of a reference cagA coding sequence, GenBank Accession No. AB057095 (SEQ ID NO: 7).

The primer set of the present invention can be an oligonucleotide primer set for amplifying a nucleotide region of the cagA gene of *H. pylori* corresponding to positions 428-624 of SEQ ID NO: 7. In an embodiment, the primer set comprises an oligonucleotide set comprising at least one oligonucleotide consisting of at least 10 contiguous nucleotides present in the nucleotide sequence as set forth in SEQ ID NO: 1 and at least one oligonucleotide consisting of at least 10 contiguous nucleotides present in the nucleotide sequence as set forth in SEQ ID NO: 2. In some embodiments, the primer set comprises an oligonucleotide set comprising an oligonucleotide consisting of SEQ ID NO: 1 and an oligonucleotide consisting of SEQ ID NO: 2.

The primer set of the present invention can be an oligonucleotide primer set for amplifying a nucleotide region of the cagA gene of *H. pylori* corresponding to positions 433-668 of SEQ ID NO: 7. In an embodiment, the primer set comprises an oligonucleotide set comprising at least one oligonucleotide consisting of at least 10 contiguous nucleotides present in the nucleotide sequence as set forth in SEQ ID NO: 3 and at least one oligonucleotide consisting of at least 10 contiguous nucleotides present in the nucleotide sequence as set forth in SEQ ID NO: 4. In another embodiment, the primer set comprises an oligonucleotide set comprising an oligonucleotide consisting of SEQ ID NO: 3 and an oligonucleotide consisting of SEQ ID NO: 4.

The primer set of the present invention can be an oligonucleotide primer set for amplifying a nucleotide region of the cagA gene of *H. pylori* corresponding to positions 431-671 of SEQ ID NO: 7. In an embodiment, the primer set comprises an oligonucleotide set comprising at least one oligonucleotide consisting of at least 10 contiguous nucleotides present in the nucleotide sequence as set forth in SEQ ID NO: 5 and at least one oligonucleotide consisting of at least 10 contiguous nucleotides present in the nucleotide sequence as set forth in SEQ ID NO: 6. In an embodiment, the primer set comprises an oligonucleotide set comprising an oligonucleotide consisting of SEQ ID NO: 5 and an oligonucleotide consisting of SEQ ID NO: 6.

The primer set of the present invention can be an oligonucleotide primer set for amplifying nucleotide regions of the cagA gene of *H. pylori* corresponding to positions 428-624, 433-668 and 431-671 of SEQ ID NO: 7. In an embodiment, the primer set comprises an oligonucleotide set including an oligonucleotide consisting of the nucleotide sequence as set forth in SEQ ID NO: 1 and an oligonucleotide consisting of the nucleotide sequence as set forth in SEQ ID NO: 2; an oligonucleotide set including an oligonucleotide consisting of the nucleotide sequence as set forth in SEQ ID NO: 3 and an oligonucleotide consisting of the nucleotide sequence as set forth in SEQ ID NO: 4; and an oligonucleotide set including an oligonucleotide consisting of the nucleotide sequence as set forth in SEQ ID NO: 5 and an oligonucleotide consisting of the nucleotide sequence as set forth in SEQ ID NO: 6.

As used herein, the term "primer" refers to a single-stranded oligonucleotide sequence complementary to a nucleic acid sequence sought to be copied and serves as a starting point for synthesis of a primer extension product. The length and sequence of a primer are determined to be suitable for initiating the synthesis of an extension product. Preferably, a primer is about 5-50 nucleotides in length. The length and sequence of a primer can be appropriately determined according to the complexity of a target DNA or RNA and the use conditions of a primer, e.g., the temperature, and ionic strength during hybridization to its complement. The primer set of the present invention was designed from a gene specific to *H. pylori*, the cagA gene, using other saliva-derived oral flora as a control. Since the genome sequences of *H. pylori* strains have high diversity, the primer set of the present invention was designed from highly conserved regions of the cagA coding sequence from 100 isolates of *H. pylori*. Genbank accession numbers of the cagA coding sequences of the *H. pylori* isolates used in the design of the primer set of the present invention are as follows: AB057096, AF222808, AB057098, AY330639, AB090088, AY330637, AF247651, AB057095, AB057072, AB057090, AB057094, AB057060, AB057070, AB057078, AB057065, AB057084, AB057075, AY330644, AB057064, AF222809, AF289439, AF289442, AF289460, AF479032, AB057074, AB057088, AB190940, AF289433, AF289433, AF289462, AF289462, AB090143, AF289457, AF289450, AF083352, AB057068, AB057085, AB057061, AF289444, AB057086, AB190956, AB190948, AB190942, AF289447, AF289447, DQ011620, AF289443, AF222807, AF289436, AB190941, AF289463, AB190951, AB090147, AB190950, AB057073, AF289458, AF289458, AF289448, AF289448, AB190953, AY330642, AY330642, AB090146, AF289461, AF289461, AF289440, AF289440, AB057089, AB057099, AF427099, AB057093, AF289452, AF289445, AF289445, AF289455, AF289455, AF289453, AF289453, DQ067454, AF282853, U60176, AF202973, AB015413, AB015416, AF001357, AB003397, AB057003, AB090090, AF289446, AB190947, AB090086, AF289434, AF289438, AF289451, AB110963, AB057071, AB015415, AB190949, AB090151, and AB057069.

Corresponding saliva-derived oral bacteria having a high frequency of occurrence were selected as the control sequences for selecting a sequence region in *H. pylori* strains specific to *H. pylori*. The control bacterial sequences present in NCBI Genbank that were selected consisted of *Acinetobacter baumanii*, *Acinetobacter calcoaceticus*, *Acinetobacter lwoffii*, *Bacillus subtilis*, *Bordetella ansorpii*, *Bordetella avium*, *Borditella bronchiseptica*, *Borditella pertussis*, *Citrobacter freundii*, *Enterobacter aerogenes*, *Enterobacter cloacae*, *Enterococcus faecalis*, *Enterococcus faecium*, *Escherichia coli*, *Gemella melitensis*, *Haemophilus aphrophilus*, *Klebsiella oxytoca*, *Moraxella nonliquefaciens*, *Morganella morganii*, *Proteus mirabilis*, *Proteus vulgaris*, *Pseudomonas fluorescens*, *Pseudomomas putida*, *Pseudomomas stutzeri*, *Salmonella typhi*, *Salmonella typhimurium*, *Shigella boydii*, *Shigella flexneri*, *Shigetla sonnei*, *Staphylococcus cohnii*, *Staphylococcus epidermidis*, *Staphylococcus gallinarium*, *Staphylococcus haemolyticus*, *Staphylococcus hominis*, *Staphylococcus intermedius*, *Staphylococcus lentus*, *Staphylococcus lugdunensis*, *Staphylococcus xylosus*, CNS, *Streptococcus agalactiae* (Group B), *Streptococcus dysgalactiae*, *Streptococcus gordonii*, *Streptococcus intermedius/milleri*, *Streptococcus mitis*, *Streptococcus oralis*, *Streptococcus pyogenes*, *Streptococcus salivarius* subsp. *thermophilus*, *Streptococcus sanguinis*, and *Streptococcus suis*.

A highly conserved sequence region in the 100 *H. pylori* strains used which possessed a mismatch of at least 11 consecutive bp relative to the above control bacterial sequences was selected, using BLAST to align the *H. pylori* sequences against the above bacterial sequences to determine regions of mismatch. The criterion for selecting an *H. pylori* sequence with a mismatch of at least 11 bp was used based on the fact that in chip hybridization, when probes on a chip are exposed to nucleic acids in a test sample, the maximum number of binding base pairs between the two without a chance of non-specific binding to the chip is 11 bp.

When performing PCR using the primer set of the present invention, a target sequence region of the cagA gene of *H. pylori* sought to be amplified is selected from nucleotide regions corresponding to positions 428-624, 433-668, or 431-671 of SEQ ID NO: 7. A primer set according to an exemplary embodiment of the present invention is presented in Table 1 below.

TABLE 1

Primer set according to an exemplary embodiment of the present invention

| Primer name | SEQ ID NO: | Remark |
|---|---|---|
| Hpy-cagA-F1 | 1 | Forward primer for amplification of nucleotide region corresponding to positions 428-624 of SEQ ID NO: 7 |

TABLE 1-continued

Primer set according to an exemplary embodiment of the present invention

| Primer name | SEQ ID NO: | Remark |
|---|---|---|
| Hpy-cagA-R1 | 2 | Reverse primer for amplification of nucleotide region corresponding to positions 428-624 of SEQ ID NO: 7 |
| Hpy-cagA-F2 | 3 | Forward primer for amplification of nucleotide region corresponding to positions 433-668 of SEQ ID NO: 7 |
| Hpy-cagA-R2 | 4 | Reverse primer for amplification of nucleotide region corresponding to positions 433-668 of SEQ ID NO: 7 |
| Hpy-cagA-F3 | 5 | Forward primer for amplification of nucleotide region corresponding to positions 431-671 of SEQ ID NO: 7 |
| Hpy-cagA-R3 | 6 | Reverse primer for amplification of nucleotide region corresponding to positions 431-671 of SEQ ID NO: 7 |

The primer set of SEQ ID NOS: 1 and 2 is used for amplification of a nucleotide region of the cagA gene of *H. pylori* corresponding to positions 428-624 of SEQ ID NO: 7, the primer set of SEQ ID NOS: 3 and 4 is used for amplification of a nucleotide region of the cagA gene of *H. pylori* corresponding to positions 433-668 of SEQ ID NO: 7, and the primer set of SEQ ID NOS: 5 and 6 is used for amplification of a nucleotide region of the cagA gene of *H. pylori* corresponding to positions 431-671 of SEQ ID NO: 7. Thus, products amplified using these primer sets are respectively 199 bp, 240 bp, and 241 bp in length.

In the specification, an oligonucleotide used as a primer may include a nucleotide analogue, e.g., a phosphorothioate, an alkylphosphorothioate, or a peptide nucleic acid, or the oligonucleotide used as a primer can be modified with an intercalating agent.

The present invention also provides a method of detecting *H. pylori* in a sample. The method comprises using genomic DNA as a template and an oligonucleotide primer set specific for amplifying an *H. pylori*-specific target sequence in an *H. pylori* cagA gene in an amplification reaction; and detecting *H. pylori* in the sample when the *H. pylori*-specific target sequence is amplified. The method can further comprising isolating the genomic DNA from a sample. In an embodiment, the *H. pylori*-specific target sequence is a nucleotide region of the cagA gene of *H. pylori* corresponding to positions 428-624, 433-668, or 431-671 of SEQ ID NO: 7. In an embodiment, the oligonucleotide primer set comprises an oligonucleotide set specific for the *H. pylori*-specific target sequence of the cagA gene corresponding to positions 428-624 of SEQ ID NO: 7, an oligonucleotide set specific for the *H. pylori*-specific target sequence of the cagA gene corresponding to positions 433-668 of SEQ ID NO: 7, and an oligonucleotide set specific for the *H. pylori*-specific target sequence of the cagA gene corresponding to positions 431-671 of SEQ ID NO: 7.

The method of the present invention includes isolating genomic DNA from a sample which may contain *H. pylori*. The sample can be saliva, a biopsy sample, blood, a skin tissue, a liquid culture, feces, urine, or the like, but is not limited to the illustrated examples. The isolation of genomic DNA from the sample can be performed using any method known in the art, e.g., using a commercially available kit such as a WIZARD® genomic DNA purification kit (Promega).

The method of the present invention includes using the genomic DNA as a template and an oligonucleotide primer set specific for an H. pylori-specific target sequence in an H. pylori cagA gene in an amplification reaction. The amplification reaction can be performed using any appropriate method known in the art, e.g., polymerase chain reaction (PCR), ligase chain reaction, nucleic acid sequence-based amplification, transcription-based amplification system, strand displacement amplification, Qβ replicase amplification, or other nucleic acid amplification methods. Among these amplification reactions, PCR is a method for amplifying a target nucleic acid from a primer pair specifically binding with the target nucleic acid using a DNA polymerase. PCR is well known in the art and can be performed using a commercially available kit.

In the method of the present invention, the amplified target sequence can be labeled with a detectable labeling material. For example, the labeling material can be a fluorescent material, a phosphorescent material, or a radioactive material, but the present invention is not limited thereto. Preferably, the labeling material can be Cy-5 or Cy-3. When the target sequence is amplified by PCR using primers which are labeled at their 5'-ends with Cy-5 or Cy-3, the amplified target sequence becomes labeled with the detectable labeling material. When performing PCR using a radioactive material, a radioisotope such as $^{32}$P or $^{35}$S is appropriately incorporated into one or more of the dNTPs present in the PCR solution, and thus, the PCR product becomes labeled with the radioisotope as the dNTPS are incorporated into the PCR product.

The oligonucleotide primer set used for amplification of the target sequence is as described above.

The method of the present invention includes detecting H. pylori in the sample when the H. pylori-specific target sequence is amplified. The detection of the amplified product of the H. pylori-specific target sequence can be performed using a DNA chip, gel electrophoresis, a radiation measurement, a fluorescence measurement, or a phosphorescence measurement, but the present invention is not limited thereto. For example, the detection of the amplified product may be performed by gel electrophoresis. The gel electrophoresis may be agarose gel electrophoresis or acrylamide gel electrophoresis depending on the size of the amplified product. With respect to fluorescence measurement, when PCR is performed using primers labeled at their 5'-ends with a fluorophore such as Cy-5 or Cy-3, the amplified target sequence is labeled with the detectable fluorescent material, and the intensity of fluorescence emitted from the fluorescent material is measured using a fluorescence spectrophotometer. With respect to radiation measurement, when performing PCR, a radioisotope such as $^{32}$P or $^{35}$S is added to a PCR solution in a form that it will be incorporated into the amplified PCR product, for example a radio-labeled dNTP, and thus, the amplified PCR product is labeled with the radioisotope. Radiation intensity can be measured using a radiation measurement machine, e.g., a Geiger counter or a liquid scintillation counter.

The present invention also provides a kit for detecting H. pylori in a sample, which includes: at least one oligonucleotide primer set according to an embodiment of the present invention; and a reagent for performing amplification. In the kit of the present invention, the reagent may include DNA polymerase, dNTPs, a buffer, and the like. The kit of the present invention may further include an instruction manual specifying optimal reaction conditions. The kit of the present invention can detect H. pylori in a sample such as saliva, a biopsy sample, blood, a skin tissue, a liquid culture, feces, or urine.

Hereinafter, the present invention will be described more specifically with reference to the following examples. The following examples are for illustrative purposes only and are not intended to limit the scope of the invention.

EXAMPLES

Example 1

Selection of Primers for Amplifying Target Sequences Commonly Found in cagA Genes of H. pylori Isolates In Example 1, target sequences in the cagA gene present in 100 isolates of H. pylori were selected, and primer sets capable of amplifying the target sequences were designed.

First, coding sequences of the cagA gene of H. pylori isolates were acquired from Genbank, and conserved regions were selected as target sequences for species-specific amplification using the program DNASTAR. The conserved regions of the cagA gene coding sequence of H. pylori selected as target sequences were the nucleotide regions corresponding to positions 428-624, 433-668 and 431-671 of SEQ ID No: 7. Subsequently, a primer set was designed to specifically amplify each of the three target sequences. The three oligonucleotide primer sets designed were: an oligonucleotide primer set having sequences as set forth in SEQ ID NOS: 1 and 2, an oligonucleotide primer set having sequences as set forth in SEQ ID NOS: 3 and 4, and an oligonucleotide primer set having sequences as set forth in SEQ ID NOS: 5 and 6, amplifying nucleotide regions corresponding to positions 428-624, 433-668 and 431-671, respectively, of SEQ ID NO: 7.

Example 2

Amplification of cagA Gene of H. pylori Using Primer Sets of the Present Invention Nucleotide regions of the cagA gene of H. pylori corresponding to positions 428-624, 433-668 and 431-671 of SEQ ID NO: 7 were amplified using the three primer sets designed in Example 1.

First, PCR was performed using genomic DNA of H. pylori isolates as templates and the three primer sets designed in Example 1 as primers to determine if each target sequence was specifically amplified.

(1) Isolation of Genomic DNA of H. pylori Isolates

Genomic DNA was extracted from H. pylori isolates using a QIAGEN bacterial DNA extraction kit.

Then, the genomic DNA was quantified, and small aliquots (10-50 ng) of the genomic DNA was used for subsequent experiments.

(2) PCR

PCR was performed using 50 μl of a PCR solution obtained by adding sterilized water to 5.0 μl of the genomic DNA (10-50 μg DNA) prepared in (1) as templates, 5.0 μl of 10× Taq polymerase buffer, 1 μl of 10 mM dNTP mix, 4.0 μl of each primer (100 μM), and 1.0 μl of Taq polymerase (5 units), as follows: initial denaturation at 95° C. for one minute; 31 cycles of denaturation at 95° C. for 5 seconds, annealing at 62° C. for 13 seconds, and extension at 72° C. for 15 seconds; and final extension at 72° C. for one minute.

Example 3

Detection of Amplified Products of cagA Gene of *H. pylori*

Figure 1:
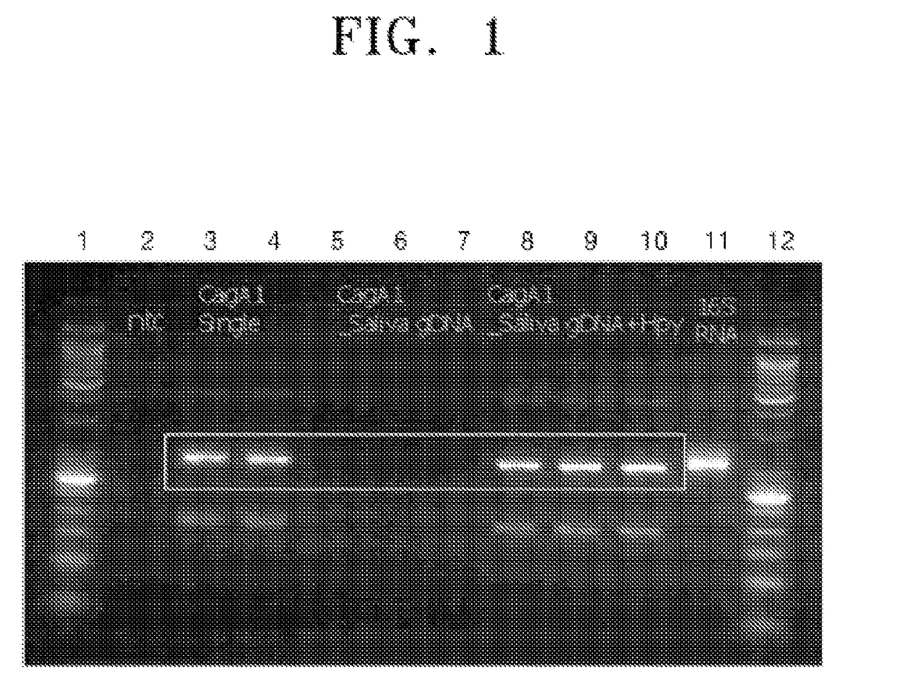
FIG. 1 is an image showing the results of electrophoretic analysis on an agarose gel of PCR products amplified from the cagA gene of *Helicobacter pylori* (*H. pylori*) by PCR using a primer set as set forth in SEQ ID NOS: 1 and 2 according to an embodiment of the present invention.
Figure 2:
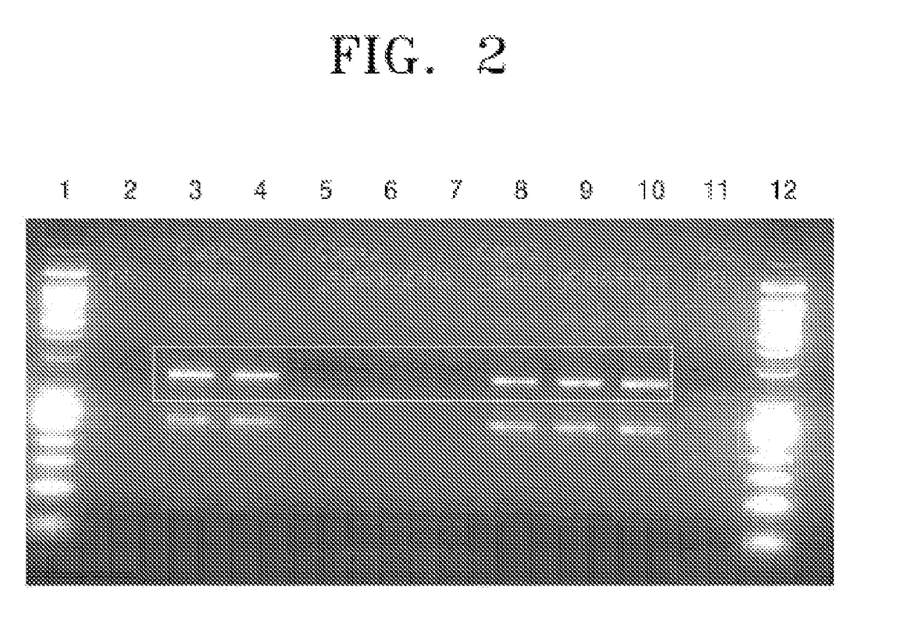
FIG. 2 is an image showing the results of electrophoretic analysis on an agarose gel of PCR products amplified from the cagA gene of *H. pylori* by PCR using a primer set as set forth in SEQ ID NOS: 3 and 4 according to another embodiment of the present invention.
Figure 3:
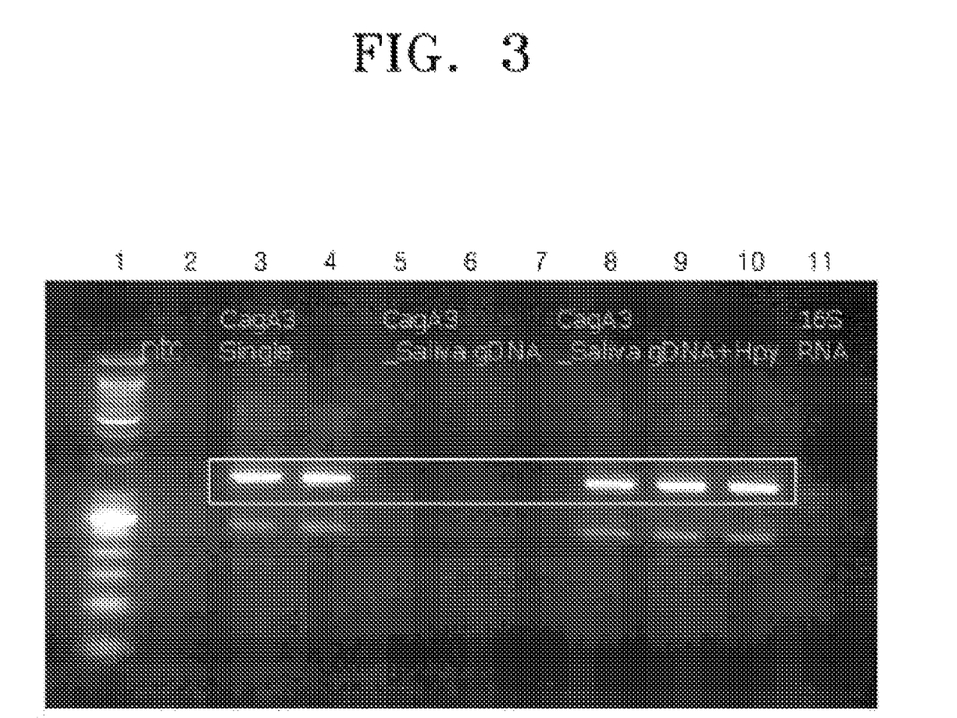
FIG. 3 is an image showing the results of electrophoretic analysis on an agarose gel of PCR products amplified from the cagA gene of *H. pylori* by PCR using a primer set as set forth in SEQ ID NOS: 5 and 6 according to still another embodiment of the present invention.

The PCR products obtained in Example 2 were analyzed using agarose gel electrophoresis. FIG. 1 is an image showing agarose gel electrophoretic results of the PCR products amplified from the cagA genes of the *H. pylori* isolates by PCR using the primer set as set forth in SEQ ID NOS: 1 and 2 according to an embodiment of the present invention, FIG. 2 is an image showing agarose gel electrophoretic results of the PCR products amplified from the cagA genes of the *H. pylori* isolates by PCR using the primer set as set forth in SEQ ID NOS: 3 and 4 according to another embodiment of the present invention, and FIG. 3 is an image showing agarose gel electrophoretic results of the PCR products amplified from the cagA genes of the *H. pylori* isolates by PCR using the primer set as set forth in SEQ ID NOS: 5 and 6 according to still another embodiment of the present invention. In FIGS. 1 through 3, lanes 1 and 12 are molecular weight size markers, lane 2 is a negative control with no template (results of PCR with no genomic DNA of *H. pylori*), lanes 3 and 4 show PCR results obtained by PCR using genomic DNAs isolated from cultures of *H. pylori*, lanes 5-7 show PCR results obtained by PCR using genomic DNAs isolated from the saliva of each of three subjects who had high digestive power (Herein, a subject who had high digestive power is a subject with a very low probability of being infected with *H. pylori*.), lanes 8-10 show PCR results obtained by PCR using genomic DNAs isolated from three samples obtained by adding *H. pylori* stains to the saliva of each of the three subjects who had high digestive power, and lane 11 is a positive control showing PCR results obtained by PCR using a primer pair (SEQ ID NOS: 8-9) specific for the 16S rRNA gene.

Referring to FIGS. 1 through 3, no band was observed in the negative control lanes. The positive control lanes showed the expected band, demonstrating that the PCR was functioning correctly. With respect to the PCR results obtained by PCR using each of the three primer sets of the present invention, specific bands (identified in each figure by the solid boxes) were observed (see lanes 3 and 4), i.e., a 199 bp band was amplified with the primer set as set forth in SEQ ID NOS: 1 and 2, a 240 bp band was amplified with the primer set as set forth in SEQ ID NOS: 3 and 4, and a 241 bp band was amplified with the primer set as set forth in SEQ ID NOS: 5 and 6. These results show that each of the three primer sets of the present invention efficiently amplified their respective target sequence in the cagA gene of *H. pylori*. (Note that the smaller fragment generated by each set of primers in the presence of *H. pylori* DNA is a dimer of the primer set which does not affect the muliplex PCR.)

PCR using each of the three cagA-specific primer sets and genomic DNA isolated from the saliva of each of the three subjects who had high digestive power, resulted in no observable product band (see lanes 5-7). This shows that the three primer sets of the present invention can discriminate *H. pylori* from oral flora. When PCR was performed using each of the three cagA-specific primer sets and genomic DNA isolated from samples obtained by adding *H. pylori* strains to the saliva of each of the three subjects who had high digestive power, the *H. pylori*-specific bands were observed (see lanes 8-10), as they were for PCR of isolated *H. pylori* of lanes 3 and 4.

The above results show that a primer set and method according to the present invention can efficiently detect *H. pylori* by amplification of its *H. pylori*-specific cagA target region. Furthermore, the primer set and method disclosed herein can also efficiently discriminate *H. pylori* from oral flora, thereby permitting use of a more readily obtained sample, saliva, instead of a biopsy sample. The compositions and detection method of the present invention permit efficient detection of *H. pylori* c with high specificity.

The terminology used herein is for the purpose of describing particular embodiments only and is not intended to be limiting of the invention. The terms "a" and "an" do not denote a limitation of quantity, but rather denote the presence of at least one of the referenced item. The term "or" means "and/or". The terms "comprising", "having", "including", and "containing" are to be construed as open-ended terms (i.e., meaning "including, but not limited to").

Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable.

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Unless defined otherwise, technical and scientific terms used herein have the same meaning as is commonly understood by one of skill in the art to which this invention belongs.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An oligonucleotide primer set, comprising:
   an oligonucleotide set comprising an oligonucleotide consisting of the nucleotide sequence as set forth in SEQ ID NO: 1 and an oligonucleotide consisting of the nucleotide sequence as set forth in SEQ ID NO: 2,
   wherein the oligonucleotide set amplifies a target sequence in a cagA gene of *H. pylori* corresponding to positions 428-624 of SEQ ID NO:7;
   an oligonucleotide set comprising an oligonucleotide consisting of the nucleotide sequence as set forth in SEQ ID NO: 3 and an oligonucleotide consisting of the nucleotide sequence as set forth in SEQ ID NO: 4,
   wherein the oligonucleotide set amplifies a target sequence in a cagA gene of *H. pylori* corresponding to positions 433-668 of SEQ ID NO:7; and
   an oligonucleotide set comprising an oligonucleotide consisting of the nucleotide sequence as set forth in SEQ ID NO: 5 and an oligonucleotide consisting of the nucleotide sequence as set forth in SEQ ID NO: 6,
   wherein the oligonucleotide set amplifies a target sequence in a cagA gene of *H. pylori* corresponding to positions 431-671 of SEQ ID NO: 7.

2. A method of detecting *H. pylori* in a sample, the method comprising:
   using genomic DNA as a template and an oligonucleotide primer set specific for amplifying an *H. pylori*-specific target sequence in an *H. pylori* cagA gene in an amplification reaction; and
   detecting *H. pylori* in a sample when the *H. pylori*-specific target sequence is amplified,
   wherein the oligonucleotide primer set is the oligonucleotide primer set defined in claim 1.

3. The method of claim 2, wherein the amplified *H. pylori*-specific target sequence is labeled with a detectable labeling material.

4. The method of claim 3, wherein the labeling material is a fluorescent material, a phosphorescent material, or a radioactive material.

5. The method of claim 2, wherein detecting *H. pylori* in the sample when the *H. pylori*-specific target sequence is amplified is performed using a DNA chip, gel electrophoresis, a radiation measurement, a fluorescence measurement, or a phosphorescence measurement.

6. The method of claim 2, wherein the amplification reaction is performed using polymerase chain reaction (PCR), ligase chain reaction, nucleic acid sequence-based amplification, transcription-based amplification system, strand displacement amplification, or Qβ replicase amplification.

7. The method of claim 2, wherein the sample is saliva, a biopsy sample, blood, a skin tissue, a liquid culture, feces, or urine.

8. A kit for detecting *H. pylori* in a sample, the kit comprising:
   the oligonucleotide primer set of claim 1; and
   a reagent for performing amplification of a nucleic acid in a sample.

9. The kit of claim 8, wherein the reagent comprises DNA polymerase, dNTPs, and a buffer.

10. The kit of claim 8, wherein the sample is saliva, a biopsy sample, blood, a skin tissue, a liquid culture, feces, or urine.

* * * * *